United States Patent
Baldenius et al.

(10) Patent No.: US 6,977,270 B2
(45) Date of Patent: Dec. 20, 2005

(54) TOCOTRIENOLQUINONE CYCLIZATION PRODUCT WITH AN ANTI-HYPERCHOLESTEROL EFFECT

(75) Inventors: Kai-Uwe Baldenius, Ludwigshafen (DE); Hartwig Schröder, Nussloch (DE); Klaus Krämer, Landau (DE); Karin Schein, Ludwigshafen (DE); Rainer Stürmer, Rödersheim-Gronau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/332,863

(22) PCT Filed: Jul. 13, 2001

(86) PCT No.: PCT/EP01/08163

§ 371 (c)(1),
(2), (4) Date: Jun. 10, 2003

(87) PCT Pub. No.: WO02/06261

PCT Pub. Date: Jan. 24, 2002

(65) Prior Publication Data

US 2004/0116715 A1 Jun. 17, 2004

(30) Foreign Application Priority Data

Jul. 14, 2000 (DE) .......................................... 100 34 233

(51) Int. Cl.[7] ..................... C07D 317/72; H61K 31/343
(52) U.S. Cl. ........................................ 514/462; 549/341
(58) Field of Search ........................ 514/462; 549/341, 549/331

(56) References Cited

U.S. PATENT DOCUMENTS

| 5,217,992 A | 6/1993 | Wright et al. |
| 5,318,993 A | 6/1994 | Pearce |

FOREIGN PATENT DOCUMENTS

| EP | 421 419 | 4/1991 |
| EP | 476 493 | 3/1992 |
| EP | 571 928 | 12/1993 |
| EP | 669 132 | 8/1995 |
| EP | 882 450 | 12/1996 |

OTHER PUBLICATIONS

Guthrie et al., 1998, Oxidants and Antioxdants . . . Molecular Mechanisms and Heath Effects, 257–264.
Qureshi, (1993) Vitamine E in Health . . . 247–267.
Brown et al., 1980, J. Jipid Rs. 21: 505–517.
Papas, 1999, CRC, Boca Raton,Fl. 189–210,Hendrich et al.
Int.J.Cancer tt, 640–645, Bennis et al.
XP0029114546.
Bichim, Biophys.Acta 1213:57–63, Gebhardt et al.
J.Pharm.Exp.Therap. 286:1122–1128,Gebhardt.
Bio.Phar.35 (6) :911–916 Aufenager et al.
Phytochemicals, 33–51, Hood.
Roempp–Lex.Chem.1999, 4572–4573.

*Primary Examiner*—Bernard Dentz
(74) *Attorney, Agent, or Firm*—Novak Druce & Quigg, LLP (57) ABSTRACT

A description is given of the use of at least one compound of the formula I

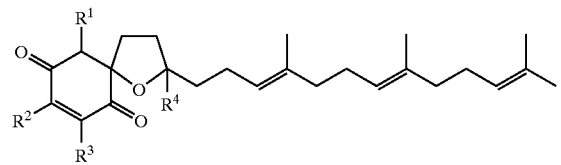

(I)

where
$R^1$, $R^2$, $R^3$ and $R^4$ independently of one another are H or $C_1$–$C_6$-alkyl; and the use of a compound of the formula I for medical use.

15 Claims, 6 Drawing Sheets

TOCOTRIENOLQUINONE CYCLIZATION PRODUCT WITH AN ANTI-HYPERCHOLESTEROL EFFECT

This application is a 371 of PCT/EP01/08163 filed Jul. 13, 2001.

The accumulation of cholesterol in the circulation and the high cholesterol and LDL cholesterol levels in plasma as a consequence of a diet which has a high content of saturated fatty acids and cholesterol is correlated with the incidence of coronary heart disease. This is one of the most frequent causes of death in industrialized countries. Hypercholesterolemia also plays a causal role in the pathogenesis of arteriosclerosis, liver cancer, xanthomatosis and many other disorders.

Effective inhibitors of cholesterol biosynthesis which are used in medicine are the statins, such as atorvastatin, fluvastatin, cerivastatin, lovastatin, mevastatin, pravastatin and simvastatin. In addition, the active compounds present in garlic extract allicin and ajoene, the compound luteolin present in artichoke extract and fibrates and the piperizine derivative BM 15.766 also exhibit cholesterol-lowering action (Gebhardt, R. et al. (1994) Biochim. Biophys. Acta 1213: 57–63; Gebhardt, R. (1998) J. Pharmacol. Exp. Therap. 286: 1122–1128; Aufenanger, J. et al. (1985) Biochem. Pharmacol. 35(6): 911–916). Palm oil is also distinguished by a cholesterol-lowering action, despite its high content of saturated fatty acids. In palm oil, tocopherols (for example vitamin E) and tocotrienols are present which have been made responsible for this action (U.S. Pat. No. 5,217, 992). Tocopherols and tocotrienols differ primarily in that tocopherols have a saturated side chain and tocotrienols, in contrast, have an unsaturated side chain which is responsible in each case for binding to lipoproteins and membranes (Hood, R. L. (1998) Phytochemicals, 33–41). Because of their antioxidant activity, tocopherols are used as compositions for the prophylaxis of oxidative damage to muscle, skin, hair, the immune system and in smokers. In addition, they are used as anticarcinogenic compounds, as nitrite traps, for example in smoked ham, and in veterinary medicine (Römpp-Lexikon Chemie [Römpp's Chemistry Lexicon] (1999), Georg Thieme Verlag, Stuttgart, 4572–4573). However, they have no effect on lipid metabolism, although for a long time the activity has been ascribed to vitamin E of preventing the oxidation of LDL cholesterol. In contrast, the tocotrienols present in palm oil are able to lower the plasma cholesterol level. The inhibitory action of γ-tocotrienol, for example, on cholesterol synthesis is due to a direct farnesylation of HMGR or to a feedback inhibition of HMGR by a farnesylated protein (Guthrie, N. and K. K. Caroll (1998), Biol. Oxidants and Antioxidants: Molecular Mechanisms and Health Effects, Champaign, AOCS-Press, 257–264; Qureshi, N. (1993) Vitamin E in Health and Disease, 247–267). A combination of γ-tocotrienol and lovastatin which acts via a different independent mechanism and whose activity is thus additive, is still more effective. To determine the effect of an active compound on the rate of cholesterol synthesis an in vitro test is used in which, when HMGR is inhibited, for example by γ-tocotrienol, decreased $^{14}$C-acetate incorporation in the microsome fraction from HepG2 cells occurs.

Palm oil and the tocotrienols present therein therefore, in birds and mammals, have an advantageous lowering action on cholesterol and LDL-cholesterol levels in plasma, without affecting the HDL level. In addition, tocotrienols decrease the apolipoprotein-B level, also a measure of the cholesterol level in blood (Brown et al. (1980), J. Lipid Res. 21:505–517). U.S. Pat. No. 5,318,993 describes a group of substances of synthetic tocotrienol analogs, ring-opened quinones, which are formed after the oxidation of tocotrienols and are distinguished in vitro ($^{14}$C-acetate incorporation into the microsome fraction of HepG2 cells) and in vivo (cholesterol and LDL-cholesterol level in hens) by an increased activity compared with tocotrienols.

The prophylactic action of tocotrienols in arteriosclerosis, in addition to the cholesterol-lowering activity, is based on the inhibition of platelet aggregation. Thus, on administration of tocotrienol, the plasma levels of thromboxan B2 and platelet factor IV decrease (Wright et al., A Symposium on Drugs Affecting Lipid Metabolism, Houston, Tex. (November 1989); Papas, A. M. (1999), CRC, Boca Raton, Fla., pp. 189–210).

Furthermore, an anticancer action is ascribed to the tocotrienols. Thus palm oil is able to prevent the formation of liver carcinomas, while a deficiency of tocotrienols in the fat tissue increases the incidence of breast cancer and skin cancer. The anticancer action of tocotrienols in liver cancer is also based on the inhibition of cholesterol synthesis and thus on a growth-inhibitory and proliferation-inhibitory activity which has been demonstrated, for example, in A549 cells (Hood, R. L. (1998), Phytochemicals, 33–51; Watkins, T. R. et al. (1999), CRC, Boca Raton, Fla., 479–496; Bennis, F. et al. (1993), Int. J. Cancer 55:640–645). However, a more important role for the anticancer action of tocotrienols is played by their 6'-OH group which, because of its antioxidant properties, acts as a free-radical trap. In addition, tocotrienols inhibit protein kinase C which can be involved, for example, in tumor development, cell proliferation and cell differentiation, platelet aggregation and free-radical release. Finally, possibly via farnesylation of ras, its carcinogenicity is prevented (Hood, R. L. (1998), Phytochemicals, 33–51; Watkins, T. R. et al. (1999), CRC, Boca Raton, Fla., 479–496). Because of these anticancer properties, tocotrienols, in combination with tamoxifen and hesperatin (flavonoids) can be used effectively for tumor prophylaxis and tumor therapy (Hood, R. L. (1998), Phytochemicals, 33–51; Guthrie, N. and K. K. Caroll (1998), Biol. Oxidants and Antioxidants, Molecular Mechanism and Health Effects, Champaign, AOCS-Press, 257–264).

It is an object of the present invention, although ring-opened quinones exhibit an improved activity compared with naturally occurring tocotrienols (U.S. Pat. No. 5,318, 993), to provide still more active synthetic analogs.

We have found that this object is achieved, surprisingly, by providing synthetic tocotrienolquinone cyclization products, termed cyclization products hereinafter, having an increased activity compared with γ-tocotrienol or the ring-opened quinones. The fact, especially, that the inventive cyclization products, even at low concentrations of $10^{-6}$ to $10^{-5}$ M (mol/l) develop a significantly high activity, was particularly surprising.

The invention relates in particular to compounds of the formula I (I)

where
$R^1$, $R^2$, $R^3$ and $R^4$ independently of one another are H or $C_1$–$C_6$-alkyl;

$R^1$ is preferably H or $CH_3$, particularly preferably H;
$R^2$ is preferably H or $CH_3$, particularly preferably $CH_3$;
$R^3$ is preferably $CH_3$ and
$R^4$ is preferably H or $CH_3$; in stereoisomerically pure form or as a mixture of stereoisomers. In addition $R^1$ can be halogens, in particular Cl.

$C_1$–$C_6$-Alkyl comprises methyl, ethyl, n-propyl and isopropyl, n-butyl, isobutyl and t-butyl, and n-pentyl and n-hexyl and their branched analogs.

The invention comprises in particular also the two diastereomers (polar/nonpolar) and the enantiomers of the compounds of the formula I. The polar diastereomer is distinguished by its being eluted from a silica gel column somewhat more slowly than the nonpolar diastereomer by a solvent mixture consisting principally of an alkane.

The invention also relates to a process for preparing a compound of the formula I, which comprises reacting a tocotrienolquinone of the formula III, (III)

where $R^1$ to $R^4$ have the meanings specified in formula I, in the presence of a catalyst to give a compound of the formula I. This produces the tocotrienolquinone cyclization product corresponding to the tocotrienolquinone used, that is to say the radicals $R^1$ to $R^4$ are predetermined by the tocotrienolquinone used.

Preferred catalysts are alkali metal carbonates, for example sodium carbonate and potassium carbonate, particular preference is given to cesium carbonate. For this, from 10 to 200 g/l, preferably 100 g/l, of a tocotrienolquinone of the formula III and from 5 to 15 g/l, prferably 10 g/l, of one of the abovementioned catalysts are dissolved in an organic solvent, preferably methylene chloride, and reacted.

The reaction can take place in customary reaction vessels, preferably glass reactors, using customary agitation and mixing apparatuses. The reaction time should be chosen so that complete conversion of the tocotrienolquinone to the corresponding cyclization product occurs, preferably from 1 to 6 hours. The reaction takes place at from about 10 to 100° C., preferably at from 20 to 50° C. Then, for example by adding n-heptane (in a ratio of 2:1, based on the volume of starting solution) and a 10% strength sodium hydrogensulfate solution (in a ratio of 1:1, based on the volume of the starting solution) phase separation may be achieved, with the cyclization product and minor components formed in the reaction being found in the organic phase.

The reaction solution or the above organic phase can, for further purification of the cyclization product, for example be concentrated by evaporation after drying over sodium sulfate and, for example, be further purified by chromatography.

For example, the desired product can be separated from minor components using a silica gel column. In this case, as mentioned above, the polar diastereomer is eluted more slowly from the column than the nonpolar diastereomer by a solvent principally consisting of an alkane. By this or corresponding chromatographic processes a partial or complete separation of the two diastereomers is achieved.

However, this is not always necessary, since both diastereomers have a high cholesterol-lowering activity.

The tocotrienolquinone of the formula III used in the inventive process can be prepared in a synthesis process starting from the inventive process described, an oxidation reaction, from the corresponding tocotrienol of the formula II (II)

where $R^1$ to $R^4$ have the meanings specified in the formula I. The radicals $R^1$ to $R^4$ of the resultant tocotrienolquinone are predetermined by the tocotrienol used. Tocotrienols can be prepared synthetically or isolated from natural sources (Khor H. T. and J. Y. Lai (1991), Biologic Oxidants and Antioxidants, AOCS Press, 267–273; Goh S. H. et al. (1991) Biologic Oxidants and Antioxidants, AOCS Press, 274–283; Qureshi N. (1993), Vitamin E in Health and Disease, 247–267). The tocotrienol is converted to tocotrienolquinone by adding an aqueous solution of an oxidizing agent, selected from cerium(IV) salts or Fe(III) salts, preferably ammonium cerium(IV) nitrate or ammonium iron(III) nitrate, at a concentration of, for example, from 2 to 5 mol of oxidizing agent/mol of tocotrienol, preferably from 2 to 3 mol/mol. The reaction can take place in all customary reaction vessels at room temperature with a reaction time of from 0.5 to 8 hours, preferably 1 hour.

The above described inventive reactions are in addition preferably carried out in an inert gas atmosphere, for example under nitrogen.

The invention also relates to the use of compounds of the formula I as food supplements. Thus, inventive cyclization products can be present in foods and drinks, or consumed before, during or after mealtimes, for example in combined preparations with other food supplements.

The present invention further comprises compounds of the formula I for medical use.

Inventive cyclization products can be used in the preparation of medicaments and food supplements for lowering the plasma cholesterol level in birds and in mammals, in particular in humans. Thus inventive medicaments are used in human and veterinary medicine and on the basis of the inventive cyclization products medicaments may be prepared which can be used for treating disorders in connection with hypercholesterolemia. In addition, inventive medicaments can also be used for preventing such disorders.

The basis of the action is possibly the inhibitory activity of the inventive cyclization products on 3-hydroxy-3-methylglutaryl CoA reductase (HMGR), the rate-determining enzyme of cholesterol biosynthesis.

In addition the cyclization products are used in the preparation of medicaments and food supplements for treating and preventing cancers.

The invention also relates to pharmaceutical compositions comprising a pharmaceutically active amount of at least one inventive compound of the formula I and at least one pharmaceutically compatible vehicle. This vehicle can, independently of the desired dosage form, be present in solid or liquid form. Preferred vehicles are starch, lactose, sucrose and edible oils.

Inventive medicaments and food supplements also comprise compositions or combined preparations of the cyclization products with other active compounds. Advantageously, as a result, the dosages of the individual active compounds can be decreased.

Preferred for use of the cyclization products for preparing a medicament for treating and preventing disorders in relation to hypercholesterolemia are compositions or combined preparations. Such combined preparations can contain other inhibitors of HMGR whose inhibitory activity is based on a comparable mechanism or different mechanism and for this reason increased effectiveness is expected. Therefore, inventive compositions can comprise as further active compounds, for example, atorvastatin, fluvastatin, cerivastatin, lovastatin, mevastatin, pravastatin, simvastatin, SRI-62320, probucol, niacin (nicotinic acid), allicin, ajoene, luteolin, BM 15.766, isoflavone, curcumin, phytosterols, n-3 PUFA, probiotics and cholesterol-lowering fibrates and their derivatives and conjugates individually or in combination. Preference for use of the inventive cyclization products for preparing a medicament for treating and preventing cancers is given to compositions or combined preparations which comprise the active compounds tamoxifen and flavonoids, such as hesperatin or the like.

Inventive medicaments, compositions and combined preparations can be in the form of tablets, granules, powders, dragees, pastilles, pellets, capsules, suppositories, gels, solutions, emulsions and suspensions for enteral and parenteral administration. In addition the inventive compounds can be present in gels, lotions and creams for cutaneous application. The cyclization products can also be present as food supplements in foods and drinks, or are combined preparations with other food supplements in the abovementioned form. Gamma-tocotrienol cyclization products can be administered at a dosage of from 0.5 to 2 000 mg/day, but also in higher or lower dosages. The precise dosage and treatment pattern will depend on the state of the patient, the severity and course of the disorder, and the disposition of the patient for this disorder and will suitably be precisely established by the treating physician. The same applies to use in veterinary medicine.

The invention will now be described in more detail in the non-limiting examples which follow and with reference to the. accompanying drawings. In the drawings

The example below describes the synthesis of the inventive compound without restricting it.

EXAMPLE 1

Synthesis of γ-tocotrienolquinone Cyclization Product (Compound of the Formula I, where $R^1$=H, $R^2$=$CH_3$, $R^3$=$CH_3$ and $R^4$=$CH_3$)

R-γ-Tocotrienol (gamma-T3, 100.0 g/0.24 mol) was dissolved in ethanol analytical grade (4 800 ml) in a 6 l glass flask equipped with disk agitator, cooler, dropping funnel and thermometer, under $N_2$ blanketing. Ammonium cerium (IV) nitrate (307.2 g/0.56 mol), dissolved in distilled water (400 ml) was added to the above solution at room temperature. This mixture was stirred for one hour at room temperature and a TLC sample was taken out. This showed complete conversion of the R-γ-tocotrienol.

The solution was then partitioned between n-heptane (800 ml) and distilled water (8 000 ml). The phases were separated and the aqueous phase extracted once more with n-heptane (800 ml). The organic phases were combined and washed twice with distilled water (2 000 ml). For improved phase separation, during the second washing acetic acid analytical grade (approximately 3 ml/approximately 0.05 mol) was added. The organic phase was then dried over sodium sulfate. By evaporation to dryness on a rotary evaporator, γ-tocotrienolquinone (104.5 g) was obtained. This was further reacted as follows.

γ-Tocotrienolquinone (104.5 g), cesium carbonate ($Cs_2CO_3$, 10.0 g/0.03 mol) and methylene chloride ($CH_2Cl_2$, 1 000 ml) were added to a 4 l glass reactor equipped with cooler, disk agitator and thermometer, under $N_2$ blanketing, and the mixture was stirred at reflux. After 5 hours, a TLC sample was taken. This showed substantial conversion, but also minor components.

n-Heptane (2 000 ml) and 10% strength sodium hydrogensulfate solution (1 000 ml/0.83 mol) were added and the mixture was stirred briefly at a relatively high rotary speed. The phases were then separated and the organic phase washed twice more with distilled water (1 000 ml). The organic phase was then dried over sodiumsulfate and by evaporation to dryness on a rotary evaporator, γ-tocotrienolquinone cyclization product was obtained (100.7 g).

Separation of the Diastereomers:

This product was chromatographed completely via a flash 150 silica gel column from Biotage. The mobile phase used was 6% ethyl acetate in n-heptane. After evaporation to dryness of the main fractions (TLC monitoring) on a rotary evaporator, γ-tocotrienolquinone cyclization product (0.12 mol; 49.4 g) was obtained. TLC of the end product showed only the two diastereomers and no minor products. Separation of the diastereomers: two adjacent chromatographic fractions each of which contained only one of the two diastereomers were also evaporated to dryness on a rotary evaporator. As a result nonpolar diastereomer (0.82 g; RF value: 0.39 (mobile phase: 30% MTB/n-heptane); rotation $[α]^{25}_D$: +2.0° (c=1, ethanol)) and polar diastereomer (0.86 g; RF value: 0.35 (mobile phase: 30% MTB/n-heptane); rotation $[α]^{25}_D$: −40.0° (c=1, ethanol)) were obtained.

$^{13}$C-NMR data of the two diastereomers (in $CDCl_3$/DMSO-$d_6$ 1:4): chemical shift in δ ppm (TMS), multiplicity (S=singlet, D=doublet, T=triplet, Q=quartet)

Diastereomer 1:

| | |
|---|---|
| 1. | 85.14 S |
| 2. | 35.83 T |
| 3. | 32.82 T |
| 4. | 85.25 S |
| 5. | 50.43 T |
| 6. | 195.13 S |
| 7. | 144.24 S |
| 8. | 144.82 S |
| 9. | 196.68 S |
| 10. | 40.33 T |

-continued

| | |
|---|---|
| 11. | 22.92 T |
| 12. | 124.17 D |
| 13. | 134.08 S |
| 14. | 39.37 T |
| 15. | 26.35 T |
| 16. | 123.94 D |
| 17. | 134.23 S |
| 18. | 39.37 T |
| 19. | 26.14 T |
| 20. | 124.17 D |
| 21. | 130.46 S |
| 22. | 25.51 Q |
| 23. | 15.69 Q |
| 24. | 15.76 Q |
| 25. | 17.50 Q |
| 26. | 25.97 Q |
| 27. | 12.53 Q |
| 28. | 13.12 Q |

Diastereomer 2:

| | |
|---|---|
| 1. | 85.25 S |
| 2. | 36.11 T |
| 3. | 32.53 T |
| 4. | 85.30 S |
| 5. | 50.69 T |
| 6. | 195.16 S |
| 7. | 144.24 S |
| 8. | 144.62 S |
| 9. | 196.39 S |
| 10. | 40.85 T |
| 11. | 22.83 T |
| 12. | 124.28 D |
| 13. | 134.26 S |
| 14. | 39.37 T |
| 15. | 26.35 T |
| 16. | 123.94 D |
| 17. | 134.23 S |
| 18. | 39.37 T |
| 19. | 26.14 T |
| 20. | 124.17 D |
| 21. | 130.45 S |
| 22. | 25.51 Q |
| 23. | 15.63 Q |
| 24. | 15.78 Q |
| 25. | 17.50 Q |
| 26. | 26.68 Q |
| 27. | 12.46 Q |
| 28. | 13.08 Q |

Gas-chromatographic Analysis

GC analysis was carried out on a 50 m CP-Sil 5/CB column (Chrompack). Temperature programme: 150° C., 3 min—15° C./min—300° C., 45 min. Injector: 280° C. Detector (FID): 300° C.

TLC Conditions:
  TLC plates: silica gel 60
  mobile phase: 30% methyl tert-butyl ether/n-heptane
  spray reagent: cerium(IV) sulfate-molybdatophosphoric acid

EXAMPLE 2

Determination of Cholesterol Synthesis in HepG2 Cells (cf. Fahrner, J. et al., Eur. J. Biochem. 213: 1067–1073 (1993); Gebhardt, R., Lipids 28: 613–619 (1993); Pill, J. et al., Z. Anal. Chem. 332: 512–513 (1985)

To detect an effect on cholesterol biosynthesis by test substances, HepG2 cell cultures were used. These cells were cultured up to confluence in 35 mm 6-well cell culture incubation dishes in DMEM medium (Gibco, Eggenstein, Germany) with 2 mM gentamin, 10% fetal calf serum, 40 U/ml of streptomycin and 50 U/ml of penicillin. Frozen cells were cultured and passaged for one week before use. The confluent cells were then incubated in serum-free Williams Medium E for 4 hours at 37° C. with the test substances. $^{14}$C-Acetate (18.5 kBq/ml; 0.5 µCi/ml) was then added to the solutions. The test substances were diluted in DMSO and used at the concentrations specified. After a further 2 hours the medium was removed, the cells were washed twice with physiological saline, transferred to distilled water and homogenized by high-frequency ultrasound (20 sec, stage 3).

Incorporation of $^{14}$C-acetate into the non-saponifiable lipid fraction (sterol fraction) was determined by the following method: 1.4 ml of homogenates were incubated with 2.8 ml of 0.5 M KOH in EtOH with shaking for 1 hour at 70° C. 2.1 ml of this mixture was applied to Extrelut® columns (Merck, Darmstadt). The neutral, lipophilic, non-saponifiable substances were eluted after 30 min by 10 ml of n-heptane into scintillation vials. The $^{14}$C activity in the samples was determined, after addition of 10 ml of scintillation solution (Ultima Gold®, Packard, Merident, Conn.) in a scintillation counter. The measured values shown are to be understood as means of three independent culture dishes per test solution. The reference value used was the incorporation of $^{14}$C-acetate in the absence of the test substances, set at 100%.

Figure 1:
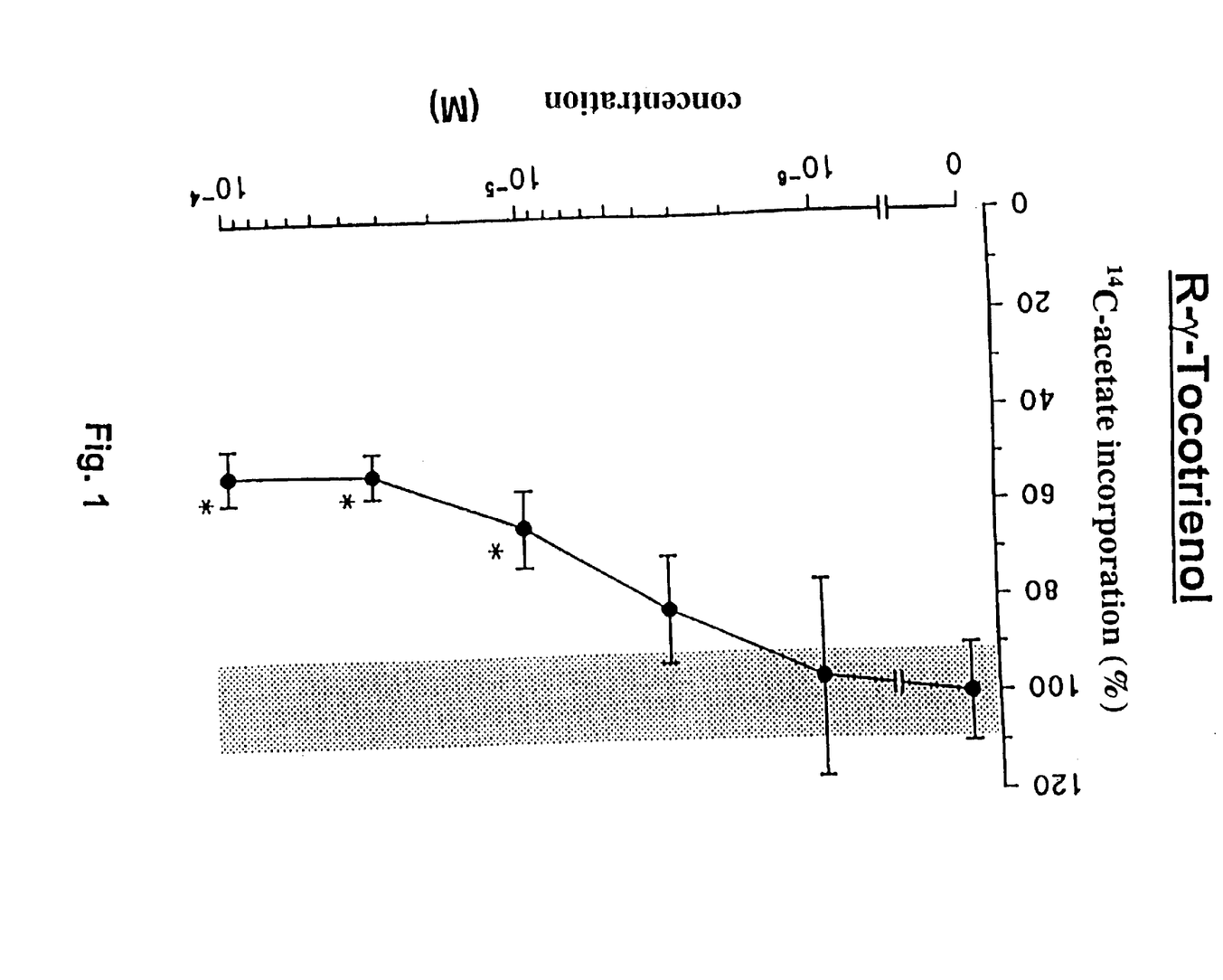
FIG. 1 shows $^{14}$C-acetate incorporation into HepG2 cells for increasing concentrations of R-γ-tocotrienol
Figure 2:
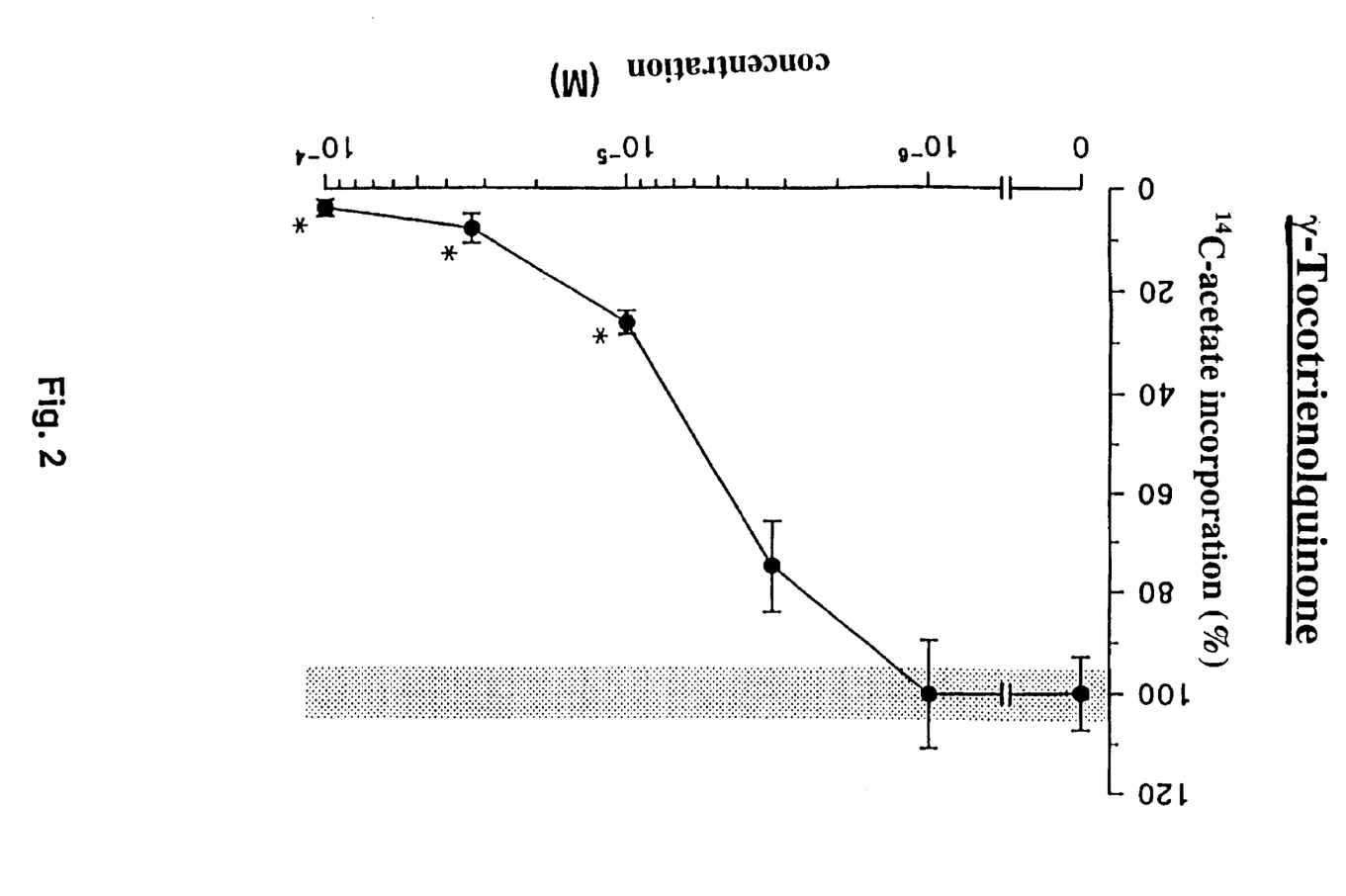
FIG. 2 shows $^{14}$C-acetate incorporation into HepG2 cells for increasing concentrations of γ-tocotrienolquinone
Figure 3:
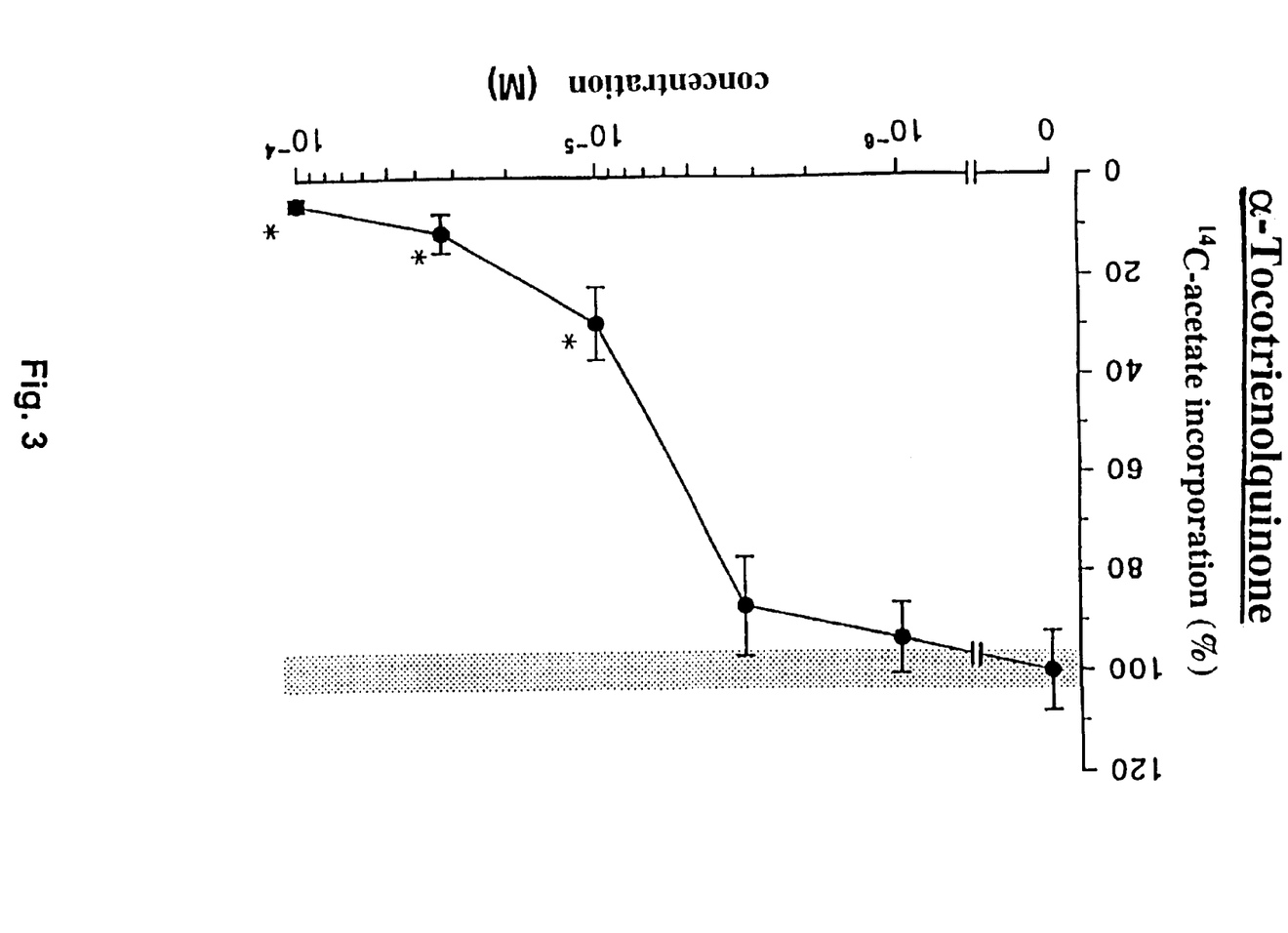
FIG. 3 shows $^{14}$C-acetate incorporation into HepG2 cells for increasing concentrations of α-tocotrienolquinone
Figure 4:
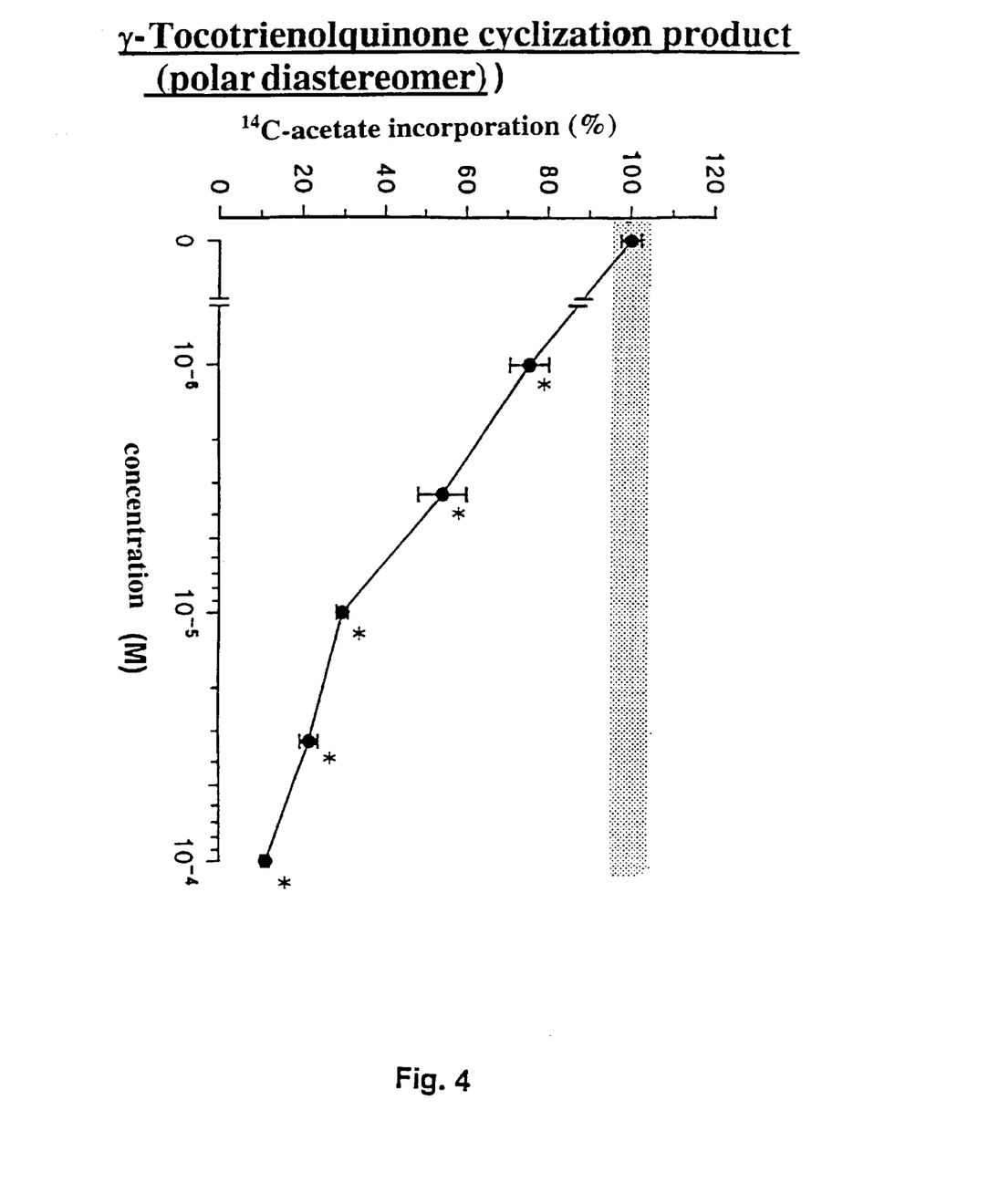
FIG. 4 shows $^{14}$C-acetate incorporation into HepG2 cells for increasing concentrations of the polar diastereomer of the cyclization product, where $R^1$ is H and $R^2$, $R^3$ and $R^4$ are each $CH_3$ (γ-tocotrienolquinone cyclization product)
Figure 5:
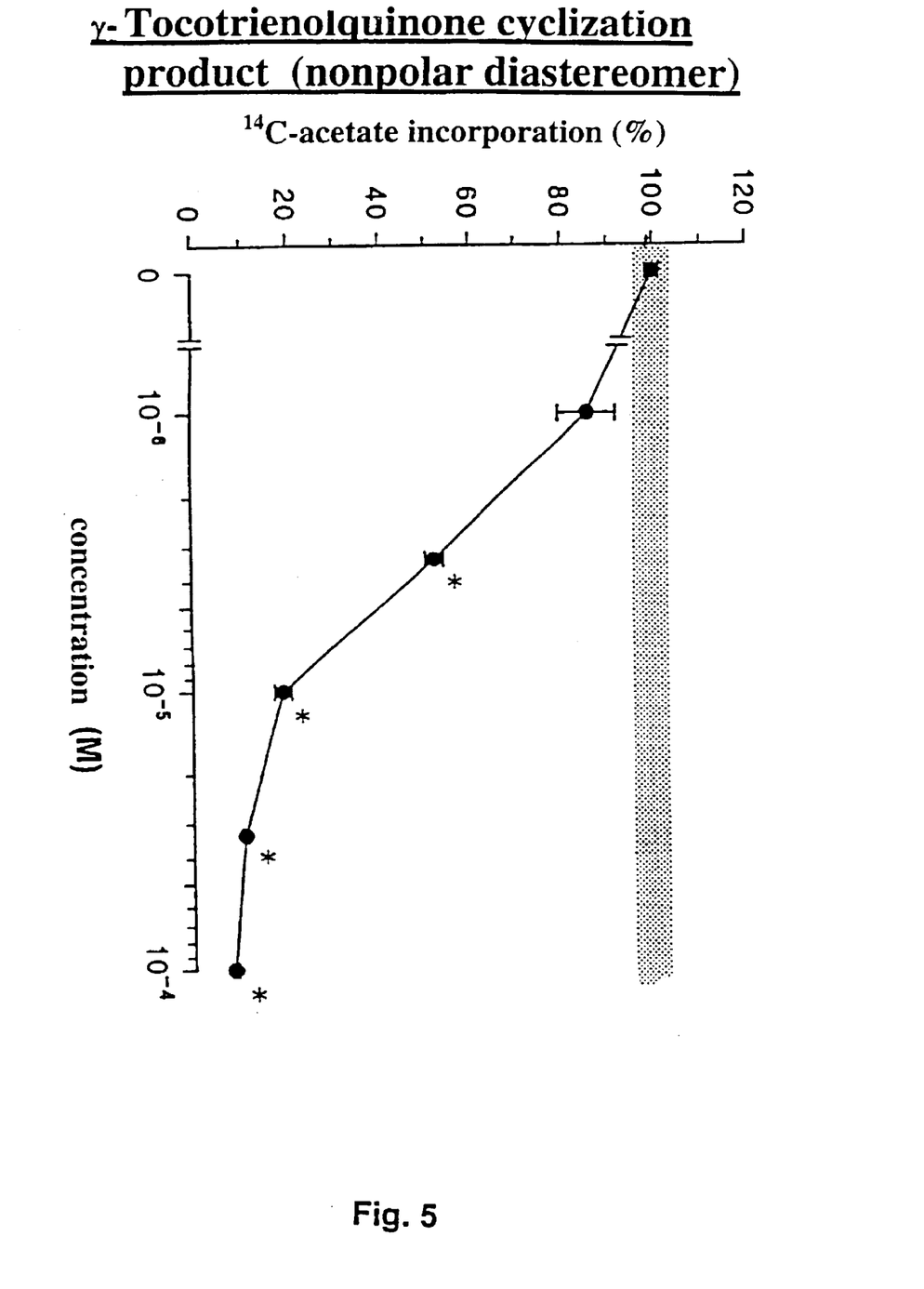
FIG. 5 shows $^{14}$C-acetate incorporation into HepG2 cells for increasing concentrations of the nonpolar diastereomer of the cyclization product, where $R^1$ is H and $R^2$, $R^3$ and $R^4$ are each $CH_3$ (γ-tocotrienolquinone cyclization product)
Figure 6:
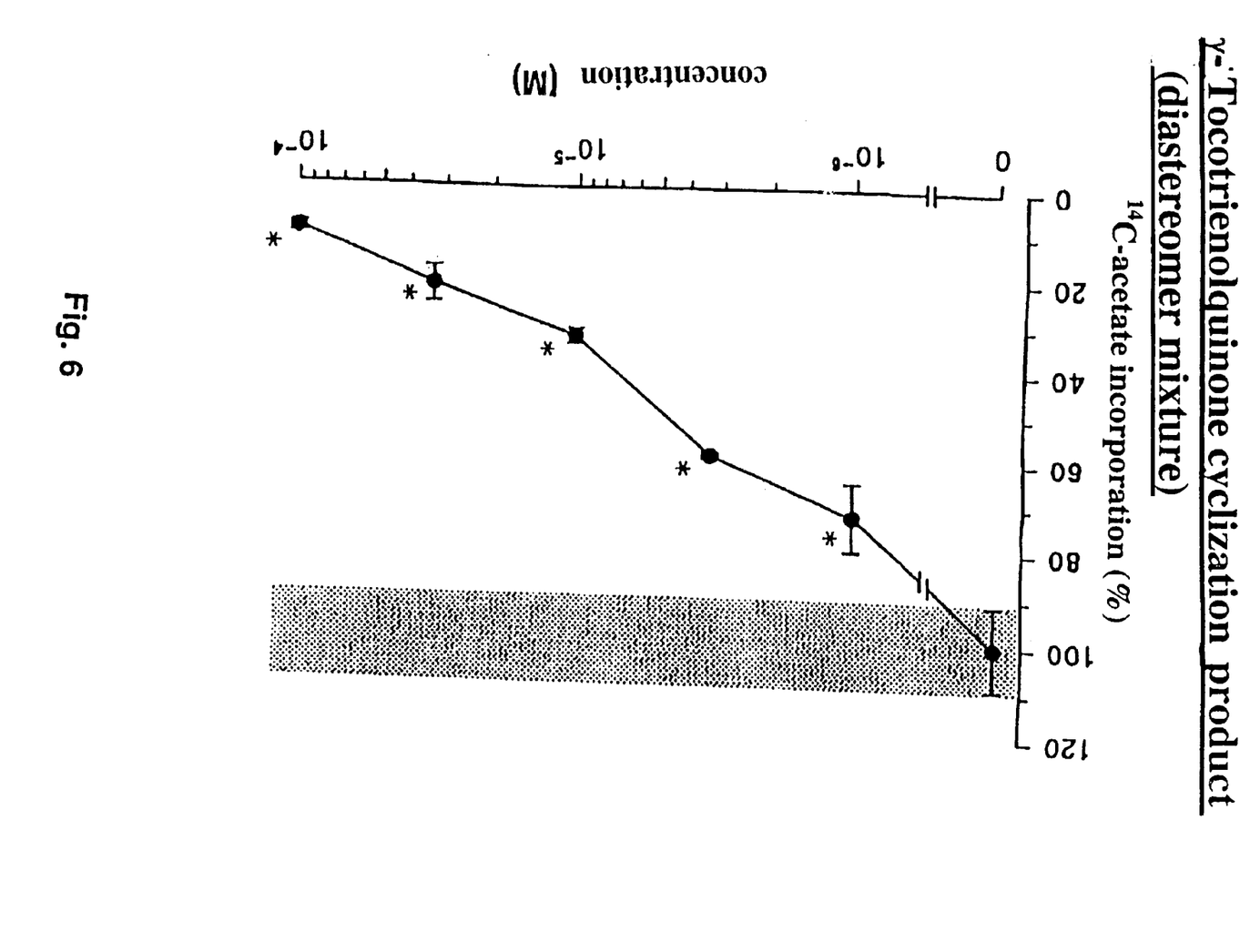
FIG. 6 shows $^{14}$C-acetate incorporation into HepG2 cells for increasing concentrations of the diastereomer mixture of the cyclization product, where $R^1$ is H and $R^2$, $R^3$ and $R^4$ are each $CH_3$ (γ-tocotrienolquinone cyclization product).

Experimental Results:

The following substances were tested in the manner specified in Example 2: R-γ-tocotrienol; γ-tocotrienolquinone; α-tocotrienol-quinone; polar diastereomer of γ-tocotrienolquinone cyclization product, nonpolar diastereomer of γ-tocotrienolquinone cyclization product, racemate of the γ-tocotrienolquinone cyclization product. The results are shown in FIGS. 1 to 6. The values given in the figures correspond to the means of three independent measured values in-each case. They are expressed in relative units based on $^{14}$C-acetate incorporation into cells, with an addition of the equivalent amount of DMSO as control. R-γ-Tocotrienol, at a concentration of $5\times10^{-6}$ M causes an approximately 20% inhibition of $^{14}$C-acetate incorporation with a maximum approximately 50% significant inhibition at concentrations $\geq 5\times10^{-5}$ M (FIG. 1). γ- and α-tocotrienolquinone cause only from a concentration of $10^{-5}$ M a significant, but approximately 70 to 75% inhibition of $^{14}$C-acetate incorporation (FIGS. 2 and 3). Both the polar and the nonpolar diastereomer of γ-tocotrienolquinone cyclization product and the mixture of the two diastereomers (1:1) cause, even at a concentration of $10^{-6}$ M, a significant 20 to 30% inhibition of $^{14}$C-acetate incorporation, at a concentration of $5\times10^{-5}$ an approximately 50% inhibition (FIGS. 4, 5 and 6). Thus the inventive cyclization products at a concentration range of $10^{-6}$ M are considerably more active than γ-tocotrienol and γ-tocotrienolquinone.

What is claimed is:

1. A compound of the formula I

(I)

where
  $R^1$, $R^2$, $R^3$ and $R^4$ independently of one another are H or $C_1$–$C_6$-alkyl;

in stereoisomerically pure form or as a mixture of stereoisomers.

2. A compound of claim 1, where $R^1$ is H or $CH_3$, $R^2$ is H or $CH_3$, $R^3$ is $CH_3$ and $R^4$ is H or $CH_3$.

3. A process for preparing a compound of claim 1 of the formula I, which comprises reacting a tocotrienolquinone of the formula III (III)

where $R^1$ to $R^4$ have the meanings specified above, in the presence of a catalyst to give a compound of the formula I.

4. A process as claimed in claim 3, wherein tocotrienolquinone of the formula III is prepared by oxidizing a tocotrienol of the formula II (II)

where $R^1$ to $R^4$ have the meanings specified above.

5. A process as claimed in claim 4, wherein the oxidizing agent is Ce(IV) salts or Fe(III) salts.

6. A process as claimed in claim 4, wherein the tocotrienol of the formula II is oxidized to the tocotrienolquinone of the formula III in an organic solvent.

7. A process as claimed in claim 3, wherein the catalyst is an alkali metal carbonate.

8. Food supplement comprising at least one compound of the formula I as claimed in claim 1.

9. A compound of the formula I as claimed in claim 1 for medical use.

10. A method for the treatment and/or the prevention of disorders in relation to hypercholesterolemia comprising administering an effective amount of a compound of the formula I as claimed in claim 1 to a patient in need thereof.

11. The method as claimed in claim 10, wherein the disorders are selected among cardiovascular disorders.

12. The method as claimed in claim 10, wherein the cardiovascular disorders are selected among arteriosclerosis, thrombosis and mycocardial infraction.

13. A method for lowering the plasma cholesterol level in humans comprising administering an effective amount of a compound of the formula I as claimed in claim 1 to a patient in need thereof.

14. A method for lowering the plasma cholesterol level in mammals or birds comprising administering an effective amount of the compound of the formula I as claimed in claim 1 to mammals or birds.

15. A pharmaceutical composition comprising at least one compound of the formula I as claimed in claim 1 and at least one pharmaceutically compatible vehicle.

* * * * *